United States Patent [19]

Giobbio et al.

[11] 4,299,962

[45] Nov. 10, 1981

[54] PROCESS FOR SYNTHESIZING 2-SULPHANILAMIDO-3-METHOXYPYRAZINE

[75] Inventors: Vincenzo Giobbio, Turin; Giorgio Ornato; Livio Buracchi, both of Ivrea, all of Italy

[73] Assignee: Pierrel S.p.A., Milan, Italy

[21] Appl. No.: 114,430

[22] Filed: Jan. 22, 1980

[30] Foreign Application Priority Data

Jan. 22, 1979 [IT] Italy .............................. 67132 A/79

[51] Int. Cl.³ .......................................... C07D 241/22
[52] U.S. Cl. .................................................. 544/408
[58] Field of Search .......................................... 544/408

[56] References Cited

U.S. PATENT DOCUMENTS 3,772,039 11/1973 Guadagni et al. .................. 544/408

OTHER PUBLICATIONS

Kirk–Othmer, "Encyclopedia of Chemical Technology", vol. 19, 1969, p. 268.

Primary Examiner—Anton H. Sutto
Attorney, Agent, or Firm—Young & Thompson

[57] ABSTRACT

2-Sulphanilamido-3-methoxypyrazine is produced in high purity and good yield, by reacting 2,3-dichloropyrazine with sulphanilamide in the presence of potassium carbonate, an aprotic solvent such as dimethylformamide and a second solvent such as toluene which is inert toward the reagents and is adapted to remove the water of reaction.

9 Claims, No Drawings

PROCESS FOR SYNTHESIZING 2-SULPHANILAMIDO-3-METHOXYPYRAZINE 2-sulphanilamido-3-methoxypyrazine is a known chemotherapeutic possessing a prolonged intense therapeutic effectiveness, with only very few negative side effects, and must be considered as among the best sulphamidic drugs. Its formula is as follows:

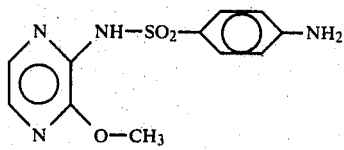

This substance has been the subject of study by numerous researchers, and has been prepared by various preparation methods, as indicated hereinafter. The said sulphamidic drug has been prepared by reacting acetylaminobenzenesulphonylchloride with 2-amino-3-methoxypyrazine followed by successive deacetylation: Camerino, Palamidessi, Brit. 928,151 (1963).

This substance has also been prepared from 2,3,5-trioxypiperazine, which is converted into 2,3,5-trichloropyrazine in the presence of phosphorus oxychloride or phosphorus pentachloride.

At this point, the procedure can follow two alternative ways, the first of which consists of treating the 2,3,5-trichloropyrazine with sulphanilamide followed by methoxidation and catalytic hydrogenation.

If the second way is followed, the 2,3,5-trichloropyrazine is treated with ammonia under pressure, then with an alkaline methylate to give 2-amino-3-methoxy-5-chloropyrazine.

It is then condensed with acetylaminobenzenesulphonylchloride, deacetylated and catalytically hydrogenated: Bernardi, Larini, Leone, Ger. 1,178,436 (1964).

A further preparation method is based on converting 2-[bis(p-acetamidophenylsulphonyl)-amino]-3-chloropyrazine to 2-(p-aminobenzenesulphanilamido)-3-chloropyrazine by heating with alkali. It is then methoxylated with methanol and sodium methylate under pressure: Neth. Appl. 6,612,171.

2-sulphanilamido-3-methoxypyrazine has also been prepared starting from 2,3-dichloropyrazine and heating with acetylaminosulphanilamide and potassium carbonate with or without the use of a solvent.

The product obtained, which is duly isolated, is 2-acetylaminosulphanilamido-3-chloropyrazine.

This substance is then heated to 120° C. under pressure for 10 hours with a mixture of sodium hydroxide and methanol to give 2-sulphanilamido-3-methoxypyrazine: Boduar, Döry, Guczoghy, Puklics etc. OE Pat. 302312.

The main object of the present invention is to provide a method for preparing 2-sulphanilamido-3-methoxypyrazine which gives a high yield and a high quality pure final product under mild and thus economical reaction conditions, without the use of dangerous substances such as sodium methylate, which is required in certain known processes.

To this end, the present invention proposes a process for synthesising 2-sulphanilamido-3-methoxypyrazine, comprising the following successive stages:

(a) - reacting sulphanilamide with 2,3-dichloropyrazine to give 2-sulphanilamido-3-chloropyrazine, which is separated and isolated;

(b) - reacting the derivative obtained in stage (a) with a mixture of methanol and sodium or potassium hydroxide, to give the final compound.

Each of these successive stages is to be considered novel. The reaction scheme for this process is as follows:

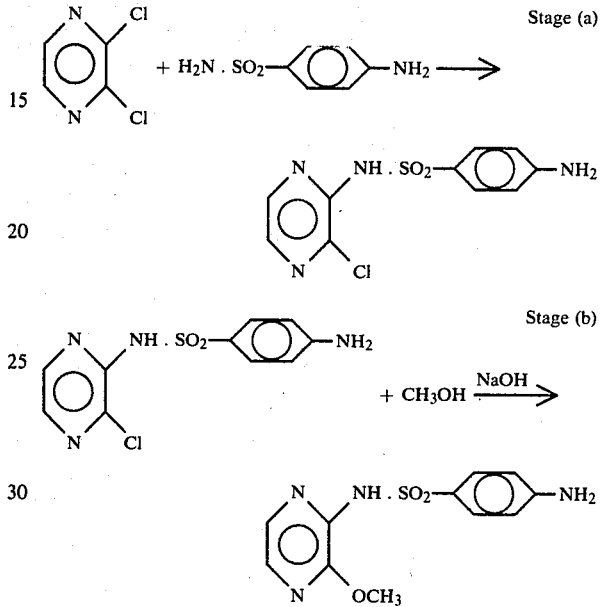

In a preferred embodiment of the process according to the invention, in said stage (a) the sulphaniliamide is mixed with 2,3-dichloropyrazine in equimolar quantities, in the presence of potassium carbonate, a solvent such as dimethylformamide and another inert solvent able to remove the water of reaction.

Dimethylacetamide, dimethylsulphoxide, sulpholane or other aprotic solvents can be used instead of dimethylformamide.

In order to obtain the best yield and a very pure final product, a further inert solvent is added, as stated, having a suitable boiling point, to make it possible to remove the water which forms during the reaction, with the aid of a phase separator. This solvent can be for example toluene.

The reaction temperature is about 120° C., and the time 5-6 hours.

At the end of the reaction, the mixture is diluted with water, filtered with carbon and the product precipitated with acetic acid.

The product is collected at the pump.

The reaction yield for stage (a) is excellent, and reaches 90–95%. The purity of the product obtained exceeds 99%.

The quantity of the aprotic solvent and the quantity of the inert solvent can vary within a range of 1 to 5 times the quantity of dichloropyrazine present, and the quantity of potassium carbonate can also vary up to 5 times the quantity of the dichloropyrazine. The temperature of the reaction under stage (a) is kept at the minimum possible value, because such a temperature gives best final product purity. Consequently, the reaction temperature range is 110°–150° C., and preferably 110°–120° C.

The reaction under stage (b) is carried out as follows: the 2-sulphanilamido-3-chloropyrazine obtained in stage (a) is mixed with methanol, a strong base such as sodium or potassium hydroxide is added, and the mixture is heated under reflux for some hours at moderate temperature.

At the end of the reaction, the mixture is diluted with water, filtered with carbon and the product precipitated with acetic acid and collected at the pump.

The characteristics of the described process will be more apparent from some embodiments of the invention, which are not to be considered limiting.

EXAMPLE 1

148 g (1 mole) of 2,3-dichloropyrazine, 172 g (1 mole) of sulphanilamide and 170 g of anhydrous potassium carbonate are placed in a flask fitted with a stirrer, reflux condenser, phase separator, thermometer and heater.

170 ml of dimethylformamide and 150 ml of toluene are then added. The mixture is heated under reflux for 6 hours, and the lower water-rich phase is collected. It is then cooled, taken up in water, filtered with carbon and the 2-sulphanilamido-3-chloropyrazine is precipitated with acetic acid, and after drying weighs 270 g, with a yield of 95% of the theoretical, and a purity exceeding 99%.

EXAMPLE 2

308 g (5.5 moles) of potassium hydroxide and 140 g (0.5 moles) of 2-sulphanilamido-3-chloropyrazine are dissolved in 945 ml of methanol.

After 3 hours of heating under reflux (about 80° C.), the mixture is cooled, and 2500 ml of water and a little carbon are added. It is filtered and acidified with acetic acid. It is cooled to 0° C. and the precipitate collected at the pump.

126 g of 2-sulphanilamido-3-methoxypyrazine are obtained with a yield of 90%.

As can be seen from these examples, the process according to the invention enables a final product of high purity to be obtained at a high yield.

Moreover, the reaction conditions used in this process are certainly mild, especially with regard to stage (b), in that a maximum temperature of only about 80° C. is attained.

The simplicity of this process relative to the analogous known syntheses described heretofore is a great advantage.

In this respect, comparison should be made with the treatment of 2,3,5-trichloropyrazine with ammonia under pressure and then with sodium methylate, which is highly dangerous; or the methoxylation of 2-(p-amino-benzenesulphanilamido)-3-chloropyrazine with methanol and sodium methylate under pressure; or the heating of 2-acetylaminobenzenesulphonamido-3-chloropyrazine with NaOH and methanol under pressure.

With particular reference to this latter process of the known art, it should be noted that the removal of the acetic and chloro group to give the final product is much more complicated when reacting a derivative of the 2-acetylamino-3-chloropyrazine type with methanol, than when reacting an intermediate such as 2-sulphanilamido-3-chloropyrazine with methanol, as described under stage (b) of the process according to the invention.

From the aforegoing, it will be noted that the process of the present invention attains the described objects by two successive reactions, each of which is to be considered novel.

Finally, it should be noted that the initial 2,3-dichloropyrazine is easily prepared from 2-chloropyrazine, this latter substance being advantageously obtainable by a process described by the applicants in Italian application No. 68488-A/78.

What we claim is:

1. A process for preparing 2-sulphanilamido-3-chloropyrazine, comprising reacting 2,3-dichloropyrazine with sulphanilamide in the presence of potassium carbonate, an aprotic solvent and a second solvent which is inert toward the reagents present in the mixture and is adapted to remove the water of reaction.

2. A process as claimed in claim 1, and reacting said 2-sulphanilamido-3-chloropyrazine with methanol and alkali hydroxide to give 2-sulphanilamido-3-methoxypyrazine, and separating the last-named product from the reaction medium.

3. A process as claimed in claim 1, in which said second solvent is toluene or xylene.

4. A process as claimed in claim 1, in which the two reagents are present in equimolar quantities.

5. A process as claimed in claim 1, in which the temperature of said reaction is 110° to 150° C.

6. A process as claimed in claim 5, in which said temperature is 110° to 120° C.

7. A process as claimed in claim 2, in which the temperature of the last-named reaction is the minimum temperature at which the reaction mixture can be refluxed.

8. A process as claimed in claim 7, in which the last-named temperature is between 70° and 80° C.

9. A process as claimed in claim 2, in which the reaction time of the last-named reaction is from 2 to 15 hours.

* * * * *